United States Patent
Rapport et al.

(10) Patent No.: US 6,739,335 B1
(45) Date of Patent: May 25, 2004

(54) METHOD AND APPARATUS FOR OPTIMIZING CONTROLLED POSITIVE AIRWAY PRESSURE USING THE DETECTION OF CARDIOGENIC OSCILLATIONS

(75) Inventors: David M. Rapport, New York, NY (US); Robert G. Norman, New Windsor, NY (US)

(73) Assignee: New York University School of Medicine, New York, NY (US)

( * ) Notice: Subject to any disclaimer, the term of this patent is extended or adjusted under 35 U.S.C. 154(b) by 0 days.

(21) Appl. No.: 09/656,746

(22) Filed: Sep. 7, 2000

Related U.S. Application Data

(60) Provisional application No. 60/152,617, filed on Sep. 8, 1999.

(51) Int. Cl.[7] ............................................. A61M 16/00
(52) U.S. Cl. ............................. 128/204.18; 128/204.21
(58) Field of Search ...................... 128/200.24, 204.18, 128/204.21, 204.23, 204.24, 203.12, 671, 672, 716, 204.26; 600/481, 484, 501, 508, 509, 529, 533, 538

(56) References Cited

U.S. PATENT DOCUMENTS

| | | | |
|---|---|---|---|
| 4,580,575 A | * 4/1986 | Birnbaum et al. | 600/484 |
| 4,655,213 A | * 4/1987 | Rapoport et al. | 128/205.25 |
| 4,982,738 A | * 1/1991 | Griebel | 600/483 |
| 5,065,756 A | * 11/1991 | Rapoport | 128/204.18 |
| 5,148,802 A | 9/1992 | Sanders et al. | |
| 5,203,343 A | 4/1993 | Axe et al. | |
| 5,245,995 A | 9/1993 | Sullivan et al. | |
| 5,335,654 A | 8/1994 | Rapoport | |
| 5,433,193 A | 7/1995 | Sanders et al. | |
| 5,479,939 A | * 1/1996 | Ogino | 600/595 |
| 5,490,502 A | 2/1996 | Rapoport et al. | |
| 5,605,151 A | * 2/1997 | Lynn | 600/323 |
| 5,704,345 A | * 1/1998 | Berthon-Jones | 128/204.23 |
| 5,803,066 A | * 9/1998 | Rapoport et al. | 128/204.23 |
| 5,862,802 A | * 1/1999 | Bird | 128/204.18 |
| 6,099,481 A | * 8/2000 | Daniels et al. | 600/538 |
| 6,138,675 A | * 10/2000 | Berthon-Jones | 128/204.23 |
| 6,223,064 B1 | * 4/2001 | Lynn et al. | 600/324 |
| 6,336,454 B1 | * 1/2002 | Farrell et al. | 128/200.24 |
| 6,363,270 B1 | * 3/2002 | Colla et al. | 600/324 |
| 6,363,933 B1 | * 4/2002 | Berthon-Jones | 128/204.23 |
| 6,409,676 B2 | * 6/2002 | Ruton et al. | 600/532 |
| 6,502,572 B1 | * 1/2003 | Berthon-Jones et al. | 128/204.23 |
| 6,532,957 B2 | * 3/2003 | Berthon-Jones | 128/204.21 |

* cited by examiner

Primary Examiner—Aaron J. Lewis
Assistant Examiner—Teena Mitchell
(74) Attorney, Agent, or Firm—Browdy and Neimark, P.L.L.C.

(57) ABSTRACT

A method and apparatus for optimizing the controlled positive pressure in treating sleep disordered breathing by using the appearance or disappearance of cardiogenic oscillation in the airway signal as an additional parameter useful for classifying the level of resistance. Ambiguities in breath monitoring can be resolved to determine whether or not breathing is labored due to an obstruction by the presence or absence of cardiogenic oscillations.

3 Claims, 5 Drawing Sheets

FIG. 6
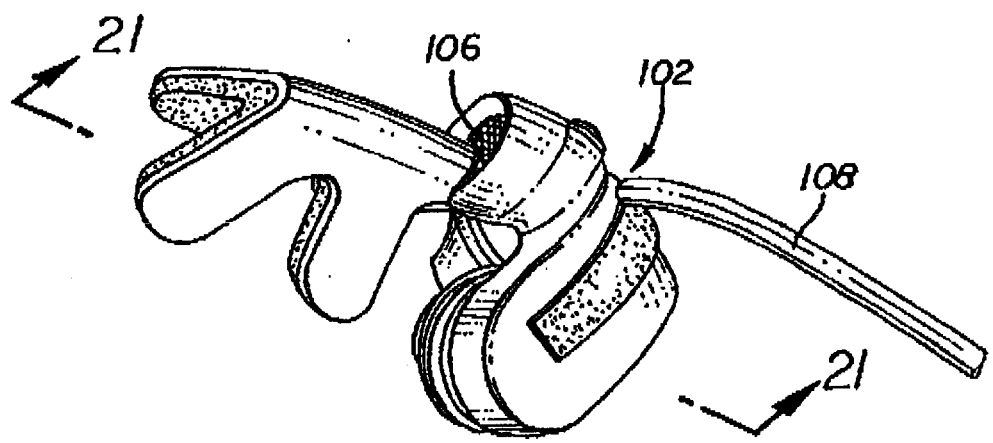
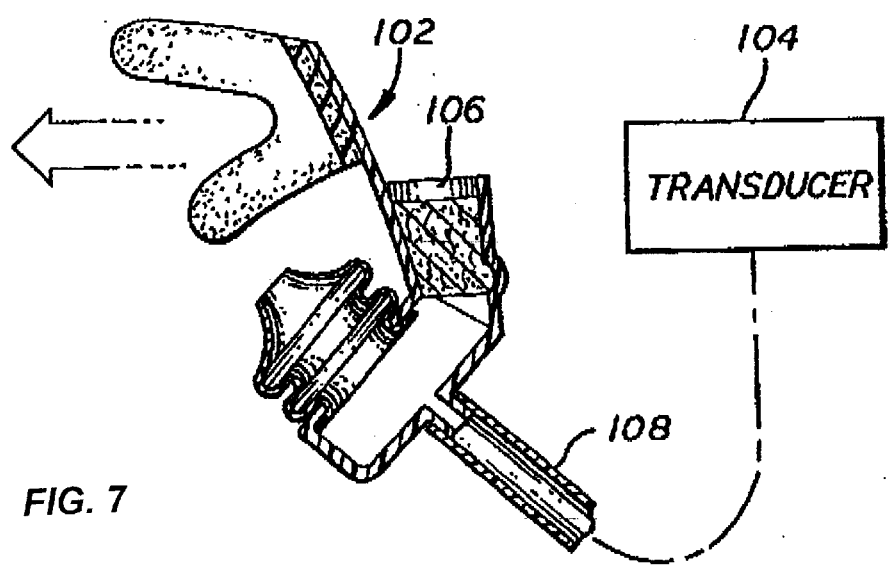
FIG. 7

METHOD AND APPARATUS FOR OPTIMIZING CONTROLLED POSITIVE AIRWAY PRESSURE USING THE DETECTION OF CARDIOGENIC OSCILLATIONS

This application claims the benefit of Provisional Application No. 60/152,617, filed Sep. 8, 1999.

FIELD OF THE INVENTION

The present invention relates to methods and apparatus for monitoring respiration to determine whether there is breathing obstruction and for titrating nasal continuous positive airway pressure based thereon.

BACKGROUND OF THE INVENTION

Obstructive sleep apnea syndrome (OSAS) is a well recognized disorder which may affect as many as 5% of the adult population. OSAS is one of the most common causes of excessive daytime somnolence. OSAS is most frequent in obese males, and it is the single most frequent reason for referral to sleep disorder clinics. OSAS is associated with all conditions in which there is anatomic or functional narrowing of the patient's upper airway occurring during sleep. The obstruction results in a spectrum of respiratory disturbances ranging from the total absence of airflow (apnea) to significant obstruction with or without reduced airflow (hypopnea and snoring), despite continued respiratory efforts. The morbidity of the syndrome arises from hypoxemia, hypercapnia, bradycardia, and sleep disruption associated with the apneas and arousal from sleep.

While monitoring respiration, it is frequently necessary to determine whether there is obstruction of breathing, whether the obstruction be manifested as apnea, hypopnea, or simply periods of high resistance which need not be accompanied by frank reduction in airflow. Identification of these events is used in both diagnosis of sleep disordered breathing and in the feedback control of automatically adjusting nasal CPAP therapy for obstructive sleep apnea syndrome. Whereas apnea and hypopnea are defined by absolute airflow, the recognition of partial obstruction can only be determined by calculating resistance. However, this generally requires invasive measurement of flow and respiratory effort, e.g., by intraesophageal pressure monitoring.

During therapeutic titration of nasal continuous positive airway pressure (CPAP) in patients with obstructive sleep apnea syndrome, residual apneas may occur that can be either obstructive or "central." Differentiating these two types of apnea, which have different physiologic as well as therapeutic implications, may impact on the adjustments made to the CPAP pressure. On the one hand, if events are obstructive it is generally assumed that a higher pressure is needed. In contrast, if the events are central, the optimal response is not clearly defined at the present time, as these apneas may be transient irregularities of breathing such as those that occur after arousal (Marrone et al (1991)) or during REM. Not increasing the pressure in the presence of these central events has been recommended as desirable as part of the titration protocol (Teschler et al (1996); Series et al (1997)). In addition, clinical experience suggests that central apneas may even occur as a reaction to excessive CPAP (Berthon-Jones et al (1996); Boudewyns et al (1998)), and this suggests the need to lower the therapeutic pressure. Alternatively, some central apneas may respond to further increases in CPAP (Issa et al (1996)). Irrespective of the decision to raise, lower or maintain the CPAP when central apnea is detected, this decision can only be made, and the impact of the decisions tested, if the apneas are correctly classified.

In addition, during treatments of other breathing disorders in sleep (hypoventilation syndromes), positive pressure is applied to the airway in such a way as to both ventilate a patient (high pressure during inspiration) and maintain the airway free of obstruction, i.e., maintain patency (low pressure during expiration). Such bilevel devices are available, for example, under the trade names BiPap (Respironics), VPAP (Resmed), and MALLINKRODT 335 (Mallinkrodt). Adjustment of this lower expiratory pressure may be dictated by decisions similar to those dictated by setting CPAP in OSAS.

By definition, both types of apnea are identified by the absence of airflow. Differentiation between them is based on analysis of respiratory effort during the apneic period. This can be done either by non-invasive methods (e.g., impedance band) or from direct but invasive measurement of intrathoracic effort (e.g., esophageal balloon). Both of these approaches rely on more than the detection of airflow alone.

Prior methods for monitoring respiration are based on a mathematical analysis technique applied to the flow signal alone during nasal CPAP therapy. This technique is illustrated in U.S. Pat. Nos. 5,335,654, 5,490,502 and 5,803,066, the entire contents of each of which being hereby incorporated by reference. Thus, it has been demonstrated that one can recognize a surrogate of high resistance in the shape of the inspiratory airflow alone. This shape is known as a "flow limitation contour" and is a characteristic flattened contour seen on the inspiratory airflow curve. An example is shown in the top curve of FIG. 8 of U.S. Pat. No. 5,803,066, in the section marked "flow limitation". It correlates highly with an elevated resistance and can be used in applications which rely on detecting abnormal behavior of the upper airway. Prior methods were based on recognition of this contour as a feedback variable for adjusting CPAP therapy.

Whereas clearly abnormal (flattened) and normal (sinusoidal) contours are readily identified, a significant number of breaths occur which are of ambiguous contour. In some individuals, these are merely variants of normal breath shapes and are not associated with partial obstruction. In other individuals, these intermediate shaped breaths are the only indication available that there is an abnormal resistance which results in clinical consequences (sleep disruption) and which requires treatment (e.g., raising the level of therapeutic CPAP). Misclassifying these breaths as to their resistance in either direction impedes optimal adjustment of CPAP therapy by either manual or automatic means.

A frequent incidental finding seen during monitoring of respiratory signals is the presence of cardiogenic oscillations (West et al (1961). These have been observed and reported during expiration as well as during apnea. Visible oscillations on the airflow signal during quiet exhalation are frequently seen during measurements made of pulmonary physiology, e.g., single breath nitrogen (Lauzon et al (1998) and diffusion studies (Brenner et al (1995). Detection of small movements at the cardiac frequency on inductive plethysmography or expired carbon dioxide signal (Kryger et al (1994)) during apnea has been suggested as an index of their "central" nature. More recently, similar oscillations have been observed on the airflow signal in adults and neonates during central apneas (Morrell et al (1995); Lemke et al (1996); Lemke et al (1998); Milner et al (1990); Shepard (1991)). Whereas Lemke et al. suggested that the presence of cardiogenic oscillations always correlated with a directly visualized open airway, Morrell et al. showed that similar oscillations were observed during central apneas regardless of the airway patency. Thus, there is no consensus on whether the presence of cardiogenic oscillations transmitted to the flow signal is dependent on patency of the airway, which can be compromised during the course of a "central" event, or on lack of respiratory effort.

In U.S. Pat. No. 5,803,066, a technique was identified to classify periods of apnea as being either obstructive or central. That patent discloses that if cardiac frequency pulsations (cardiogenic oscillations) can be detected on the airflow signal during such a period of apnea, the apnea is always classified as central. This implies that the apnea is never obstructive if cardiogenic oscillations are present.

SUMMARY OF THE INVENTION

The present invention provides a method for optimizing the controlled positive pressure in treating sleep disordered breathing by using the appearance or disappearance of cardiogenic oscillation in the airway signal as an additional parameter useful for classifying the level of resistance.

The present invention also provides a method for resolving an ambiguity in breath monitoring to determine whether or not breathing is labored due to an obstruction, by the presence or absence of cardiogenic oscillations.

According to the present invention, identification of inspiratory flow limitation can be accomplished with improved accuracy even when the breaths show a shape which is intermediate between definitely abnormal shape (flow limited) and definitely normal sinusoidal shape. This is accomplished by further examining whether there is cardiogenic oscillation present during expiratory periods and between breaths. This is detected by signal processing to enhance and identify small oscillations in the flow signal in the range of the pulse frequency in the range of the pulse, which oscillations represent cardiogenic oscillations. When these oscillations are detected, and breath whose shape is possibly abnormal, i.e., ambiguous, the breath may be classified as normal. When oscillation is absent, the threshold of the parameters used to classify the the shape of the inspiratory airflow abnormal is lowered and the breath is classified as having a high resistance. This technique is used to make the decision as to whether therapeutic CPAP pressure needs to be raised for obstructive events. It has the benefit of avoiding false positive detection of abnormally shaped breaths causing excessive rise in pressure in those patients who have them, while not sacrificing sensitivity to abnormal events in those who are more classical.

The inspiratory flow signal, both amplitude and contour, and the presence or absence of cardiogenic oscillations on the flow signal are used to define the state of resistance of the upper airway. Once the extent of obstruction is determined, appropriate adjustments are made to the CPAP pressure.

The present invention is an improvement on the method described in U.S. Pat. No. 5,803,066, by resolving ambiguities in the air flow path shape analysis. If the air flow pattern is ambiguous, and there are cardiogenic oscillations in the inter-breath period, then the breath is classified as having no obstruction, and treatment is provided based upon no obstruction. However, if the air flow pattern is ambiguous, and there are no cardiogenic oscillations, then the breath is classified as having an obstruction and treatment is provided based upon the presence of an obstruction.

The present invention may also be used to resolve ambiguities in other methods of determining the presence of an obstruction, such as use of the snoring method. If there is an ambiguous snore, which might be caused, for example, by other noise in the room, etc., the presence of oscillations would cause one to resolve the ambiguity against obstruction.

In accordance with the present invention, an apparatus for treating obstructive sleep apnea is provided, comprising a source of air and means for directing an air flow from the source to a patient. This part of the system may be of the type disclosed, for example, in U.S. Pat. No. 5,065,756, the entire contents of which being hereby incorporated by reference.

Rapoport, in U.S. Pat. No. 5,065,756, discloses a source of air and means for directing an air flow from the source to a patient. As shown in FIG. 2, a mask 40 suitable for fitting over the nose of the patients, includes a nose piece 10 and rim 11 for sealing the mask to the face. Thus, the air cuff seal 11 is made of a lightweight plastic material and must be non-irritating since it is in continuous contact with the patient's face. The nosepiece 10 is made of a partially rigid and partially flexible material, such as heavy vinyl, of a nature that can conform to the face of the patient. The element must be sufficiently large to accommodate the noses of all patients who may employ the mask. The partial rigidity is required so that the nosepiece will generally maintain its shape in use, while still enabling it to conform to the face of the patient.

A harness 42 maintains the mask in position on the patient when the apparatus is used. In this arrangement, the mask 40 is connected directly to a compressor or blower 44 by a hollow flexible tube 46. An adjustable relief valve 48 is connected between the blower 44 and the mask 40 at a T fitting 50 inserted into the tube 46. The valve is mounted by any convenient conventional means at a location separate from the patient and mask, the flexible tube being sufficiently long that fixed mounting of the valve has no effect on the patient's movements.

As illustrated in FIG. 3, the valve may be simply comprised of a rigid valve disk 51 held adjacent a valve seat 62 formed on one end of the T fitting 50. The disk 30 may be loosely axially guided at its edge by an enlarged diameter end extension 63 on the end of the T fitting 50. The valve disk 61 is urged toward the valve seat 62 by a spring, such as a helical spring 64 extending through the T-fitting 50 to a fixed connection, for example, to a pin 65 held to the walls of the T fitting. Adjustability of the pressure maintained by the valve may be affected la connecting the end of the spring 64 to the end of an adjustment screw 66 threaded in the disk 61. The adjustment of the screw thereby controls the tension of the spring, to determine the pressure of air directed to the mask. The valve is settable to enable the production of an operating pressure range within the mask of from about 5.0 to about 15.0 centimeters $H_2O$. The pressure adjustment for any patient is set so that under normal breathing conditions the valve is always open, even during inhalation. As a result, the required positive pressure is always present to maintain the nasopharyngeal airway opened.

It is of course apparent that the illustrated valve constitutes only the preferred embodiment thereof, and that other constructions thereof for serving this function may alternatively be used in accordance with the present invention. The valve 48 continually discharges gases to the external atmosphere as indicated by the arrows 70 when the blower 44 provides a positive pressure in the system. The valve 46 is suitable to maintain a positive pressure within the system of about 5 to about 15 centimeters of water, with a discharge of air flow from the valve 48 in the range of 30 to 50 liters per minute.

A reservoir bag 54 connected to the flexible tube 46 between the valve 48 and the blower 44 serves to reduce transience in the flow rate and pressure within the system.

As illustrated in FIGS. 2 and 4, the mask 40 includes ports, preferably two ports 56 passing through the shaped portion 10 of the mask 40. Through these ports 56 air from the system, and particularly air exhaled by the patient, passes from the system to the external ambient environment. These ports 56 constitute intentional leaks at the mask, and must be small enough not to vent off all the pressure delivered by the compressor 44/valve 48 combination, but must be large enough to vent the patient's expired breath over the period of expiration. For example, holes which are individually capable of passing a flow of 5 to 7 liters of air per minute with an internal mask pressure of 5 centimeters of water, and which have a diameter on the order of 1/16 inch thick, have been found satisfactory. Suitable means for blocking one or both of these ports, such as plugs 57, may be provided in order to enable adjustment of the rate of air discharge form the mask. It is of course apparent that the invention is not limited to this size and number of ports.

When the pressure within the mask is at the low end of the operating range, that is, in the range of about 5–7 centimeters of water, at least two ports 56 with sizing as described above are left open to vent the mask at a rate of approximately 10–12 liters per minute. When the pressure within the mask is sent in the upper end of the range, form about 10–15 centimeters of water, alone hole is plugged, while the other provides a vent which delivers on the order of 5–7 liters per minute.

Since the valve 48 is not mounted on the mask, but is coupled thereto by a flexible tube, the weight of the mask assembly that must be supported on a patient's face is substantially reduced, and the comfort to the patient is accordingly greatly increased. The connected between the tube 46 and the mask 40 may be via a swivel joint 58, if desired, to permit the patient to have more freedom of movement without the danger of entangling the mask apparatus with the bedding or causing the mask to separate from the face.

The compressed air may be provided by any conventional device, so that the patient may inexpensively provide this source for use in his own home. It is preferred, however, that a blower be provided instead of a compressor, since compressors tend to desiccate the air supply, while blowers deliver air at room humidity, can handle ultrasonically humidified air, and drop flow upon increases in back pressure. This latter feature is desirable, since the flow from a blower quickly increases during inspiration, when the back pressure increases in the system. The compressed air may be heated and humidified by conventional devices.

In addition, apparatus is provided for sensing the waveform of the airflow, to detect deviations therein that correspond to flow limitation in the air supplied to the patient, as well as apparatus for detecting cardiogenic oscillations to detect whether or not there is obstruction when the waveform detected is ambiguous. The deviations detected include deviations from a substantially sinusoidal waveform, flattening, or the presence of plateaus in the portions of the waveform corresponding to inspiration of the patient. In response to such variations in the airflow, the system of the invention increases or decreases the pressure to the patient in a known manner.

The method of the present invention provides for increasing the controlled positive pressure to the patient in response to the detection of flow waveform portions corresponding to flow limitations in the patient airway in response to variations in the airflow combined with the presence or absence of cardiogenic oscillations. The pressure increases may be effected periodically. Similarly, the controlled positive pressure may be periodically decreased in the absence of flow limitation or obstruction. The system may be provided with a program that periodically decreases the controlled positive pressure in the absence of detection of flow limitation or obstruction in the patient airway, and that periodically increase the pressure in the presence of detection of flow limitations classified as obstructions.

The first step in determining whether to increase or decrease the controlled positive pressure is to detect the presence of a valid breath and store an inspiratory waveform of that breath for further analysis. Next, the waveform of the stored breath is analyzed regarding its shape for presence of flow limitation. Whether flow limitation is present is in part determined by flow limitation parameters calculated from the shape of the waveforms of the current breath and of the immediately preceding breath. Once the presence of flow limitation has been analyzed, the system determines what action to take for adjustment of the controlled positive pressure. Where the waveform is ambiguous, the system determines if there is cardiogenic oscillation. If cardiogenic oscillation is present, there is no obstruction and no measures need to taken to overcome this obstruction. However, if cardiogenic oscillation is not present, there is obstruction, and the system is programmed to take appropriate action to overcome the effects of the obstruction.

An example of a breathing device or apparatus consists of a flow generator, such as a variable-speed blower, a flow sensor, an analog to digital converter, a microprocessor, and a pressure controller, such as a blower motor speed control circuit, a patient connection hose, a nasal coupling, and, optionally, a pressure transducer. Alternative patient circuits may be used, such as those disclosed in U.S. Pat. No. 4,655,213 and U.S. Pat. No. 5,065,756, the entire contents of which being hereby incorporated by reference.

One alternative patient circuit as shown in Rapoport, U.S. Pat. No. 4,655,231, includes a nose mask incorporating a threshold valve, wherein the air pressure continually applied to the mask is continually released form the mask, by means of a valve, at such a pressure that normally some pressurized air always escapes from the mask by way of the valve, at such a pressure that normally some pressurized air always escapes from the mask by way of the valve. This maintains the air pressure at the nose, in order to maintain the nasopharyngeal airway open, as well as to provide a continuous flow of fresh air to the mask so that the patient may exhale through the mask, with the exhaled air being immediately exhausted through the valve.

In one embodiment of the present invention, the blower supplies air through the flow sensor to the patient via a hose and nasal coupling. The microprocessor obtains the flow waveform from the digitized output of the flow sensor. The microprocessor then adjusts the speed of the blower via the motor control circuit to change the air pressure in the patient supply hose. A pressure transducer may be provided to measure the actual pressure in the patient hose. The microprocessor may store measured pressure and flow waveform values in its data memory to provide a history for real-time or off-line processing and analysis. When the waveform is ambiguous, the pressure or absence of cardiogenic oscillations is determined and appropriate action for the patient is taken.

BRIEF DESCRIPTION OF THE DRAWINGS

FIG. 6 is a perspective view of a nose fitting for diagnostic use.

FIG. 7 is a partial cross-sectional view of a nose fitting for diagnostic use.

DETAILED DESCRIPTION OF THE INVENTION

Figure 1:
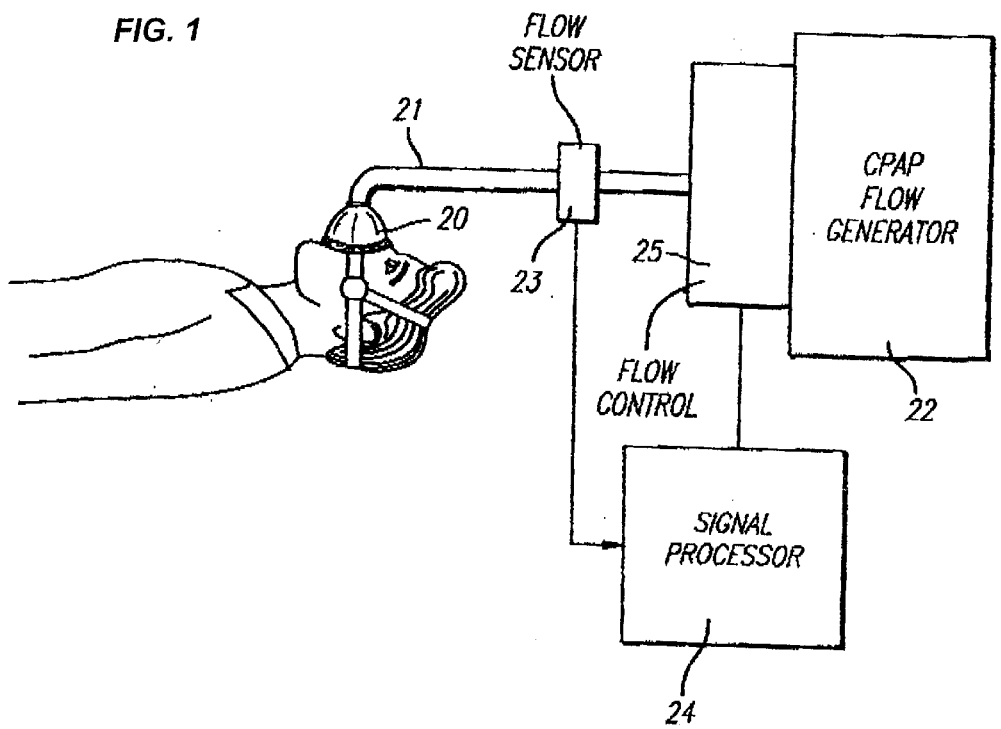
FIG. 1 illustrates an apparatus for treating sleep apnea according to the present invention including a microprocessor for adjusting the speed of the blower.
Figure 2:
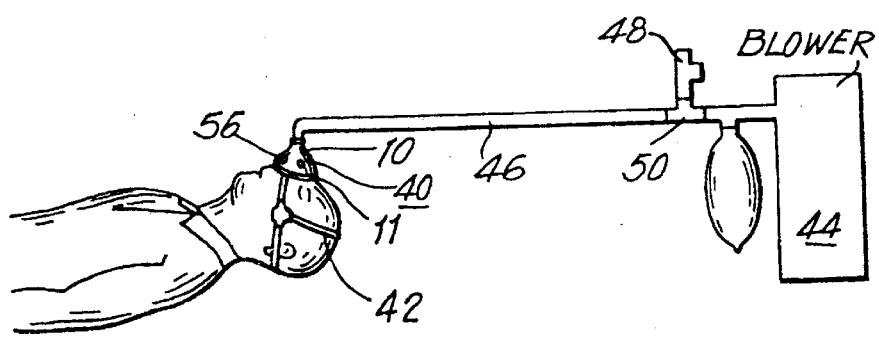
FIG. 2 is a simplified illustration of an apparatus for treating sleep apnea.
Figure 3:
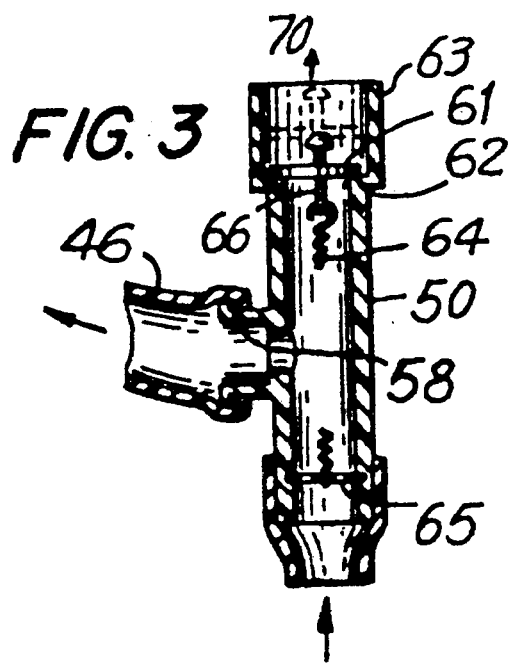
FIG. 3 is a cross sectional view of a relief valve that may be incorporated in the apparatus of FIG. 2.
Figure 4:
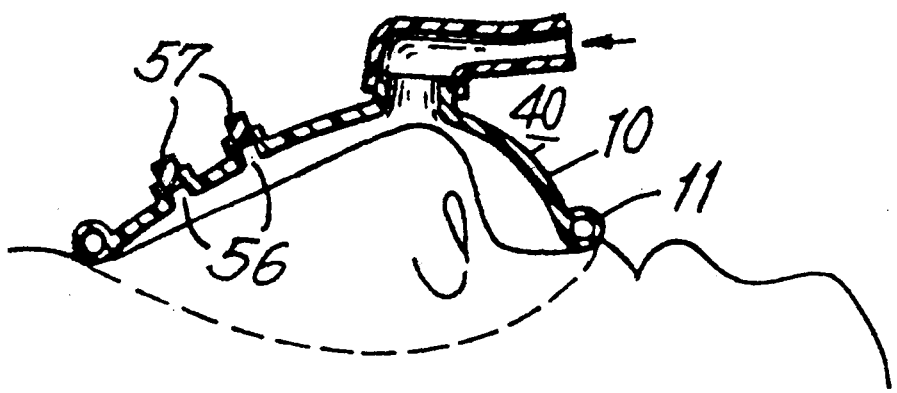
FIG. 4 is a cross-sectional view of a mask that can be used in the apparatus of FIG. 2.

During an experiment aimed at differentiating central from obstructive apnea by detecting cardiogenic oscillation during apnea, it was noted that cardiogenic oscillations occurred during expiration whenever there was a documented low resistance of the airways. See Ahmed et al, 1997.

During an experiment aimed at differentiating central from obstructive apnea by detecting cardiogenic oscillation during apnea, it was noted that cardiogenic oscillations occurred during expiration whenever there was a documented low resistance of the airways. See Ahmed et al, 1997.

This experiment showed that detection of cardiogenic oscillations on the airflow signal during CPAP titration is a very specific (100%) and a moderately sensitive (60%) indicator of central apnea as defined by the usual clinical criteria (a cessation of airflow during which no thoracoabdominal movement is seen). The high specificity and high positive predictive value may have important implications for the development and testing of algorithms used in automated titration of CPAP, where only the airflow signal is readily available. Thus, one can raise, lower, or maintain CPAP when a central apnea is identified. A critical step in all of these is to differentiate central from obstructive events if the responses are to be different.

The sensitivity and specificity of the use of cardiogenic oscillation to identify central apneas depends on the reference classification of each apnea. Misclassification of a truly obstructive apnea as central, due to insensitive detection of thoracabdominal motion, could have contributed to the lower (60%) sensitivity found, but might have artificially raised the specificity. Thus, it has been found that identifying the presence or absence of cardiogenic oscillations has diagnostic utility for classifying apneas during CPAP titration.

There is continuing debate as to the mechanism of transmission of cardiogenic oscillations seen on the airflow signal. Lemke et al. (1998) concluded that oscillations were always present in awake subjects when the airway was seen to be patent by direct visualization, and usually present in neonates thought to have central events. Obliteration of oscillations occurred during obstructive events. They concluded that cardiogenic oscillations were an indicator of airway patency, but did not verify this during sleep. The absence of cardiogenic oscillations during all obstructive apneas in the data presented above agrees with these findings. Morell et al. (1998) examined only central apneas and concluded that there was no relationship between cardiogenic oscillations and airway patency. These studies suggest two different ways to explain the 60% sensitivity of finding cardiogenic oscillations in central apnea. First, in accord with Morrell's observations, cardiogenic oscillations may not always occur in the airflow signal, even when the airway is patent. Alternatively, in accord with Lemke's observations, the central apneas seen in the present study may have been a mixture of open and closed airway central events; the 60% sensitivity may represent the percentage of events with an open airway. The present data do not permit addressing whether cardiogenic oscillations are present in an unspecified subset of central apneas or are markers of a patent airway, but suggest that their presence is an indicator of central apnea whether or not the airway is patent.

If patency of the airway, as opposed to lack of respiratory effort, were the reason for the presence of cardiac oscillations, one would predict that there would be a relationship between the level of positive pressure in the airway during CPAP, which should splint (Popper et al (1986)) the airway open at higher pressures, and the occurrence of cardiogenic oscillation during central apnea. However, this correlation was not found.

The data of this experiment lead to the speculation that transmission of cardiogenic oscillations to the airflow signal may be affected by relaxation of respiratory musculature, in addition to being influenced by patency of the airway. Thus, high muscle tone during respiratory efforts may alter coupling between the changes in volume due to cardiac contraction and volume changes in the airway. In support of the importance of muscle tone is an ancillary finding in these data: during quiet breathing, cardiogenic oscillations frequently appear at end expiration and disappear during inspiration or increase in respiratory effort (e.g., at arousal). The mechanisms of coupling appear to be complex, and transmission of cardiogenic oscillations to the flow signal at the nose or mouth could even occur outside of the thorax, e.g., from major vessels in the neck to the upper airway, above the site of obstruction. This would provide a mechanism by which muscle tone could influence transmission.

Thus, detecting the presence of cardiogenic oscillations on the CPAP flow signal is a useful indicator of non-obstructive central apnea. This finding is used to improve algorithms used in automated CPAP titration.

Specific apparatus for therapeutically titrating CPAP in patients with apnea are disclosed in U.S. Pat. No. 5,803,066, As illustrated in FIG. 1, a CPAP mask 20 with a leak pot 19 is connected via tube 21 to receive air from a CPAP flow generator 22. Any conventional CPAP system may alternatively be used. A conventional flowsensor 23 is coupled to the tube 21 to provide an electric output signal corresponding to the waveforms of conditions that indicate flow limitation. The signal processor 24 outputs a signal to a conventional flow control 25 for controlling the pressure applied by the flow generator to the tube 21. It is of course apparent that, depending upon the type of flow generator 22, the signal processor may directly control the flow generator, instead of controlling a flow control device 25.

Figure 5:
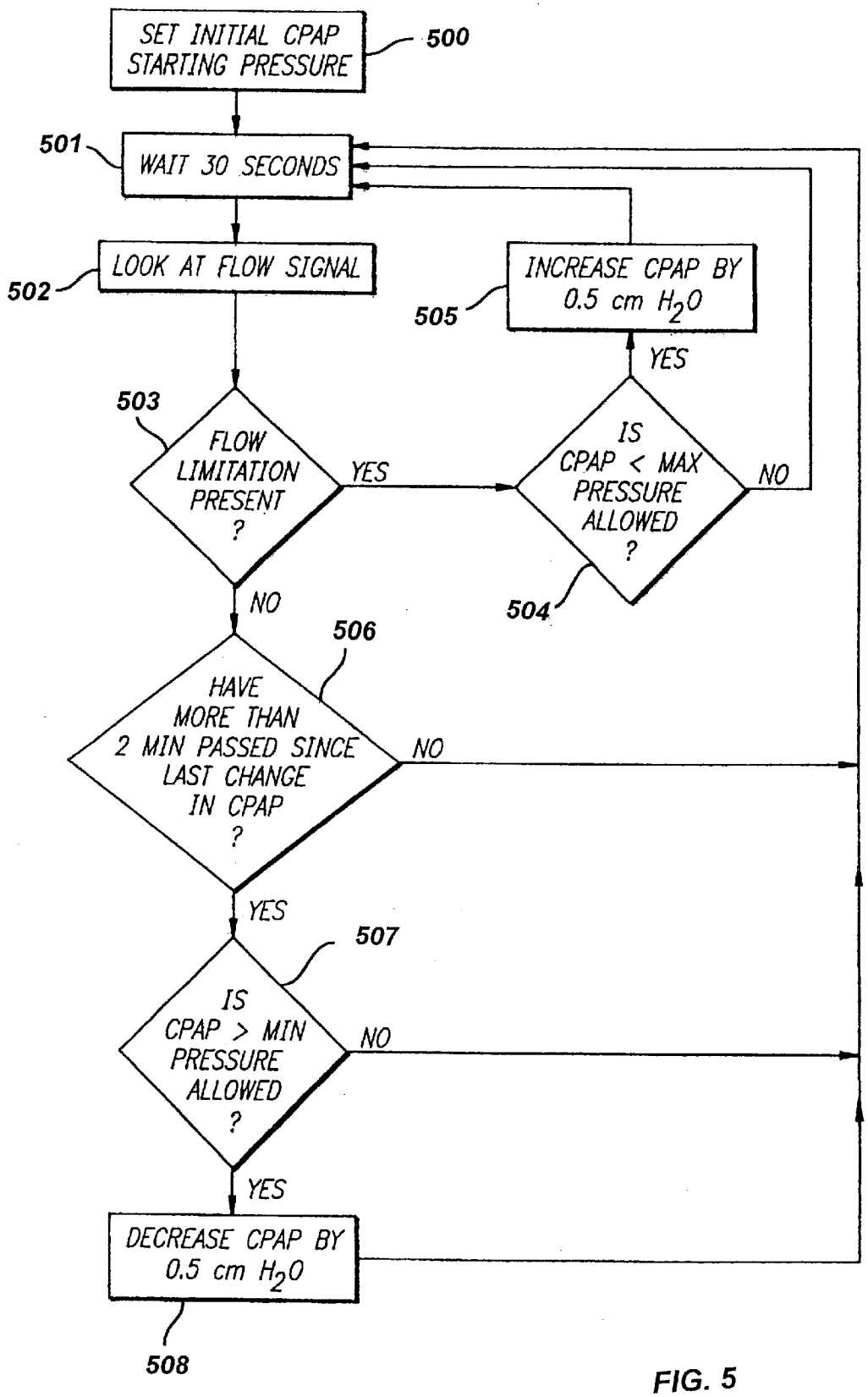
FIG. 5 is a flow diagram illustrating one technique for adjusting the CPAP pressure.
Figure 8:
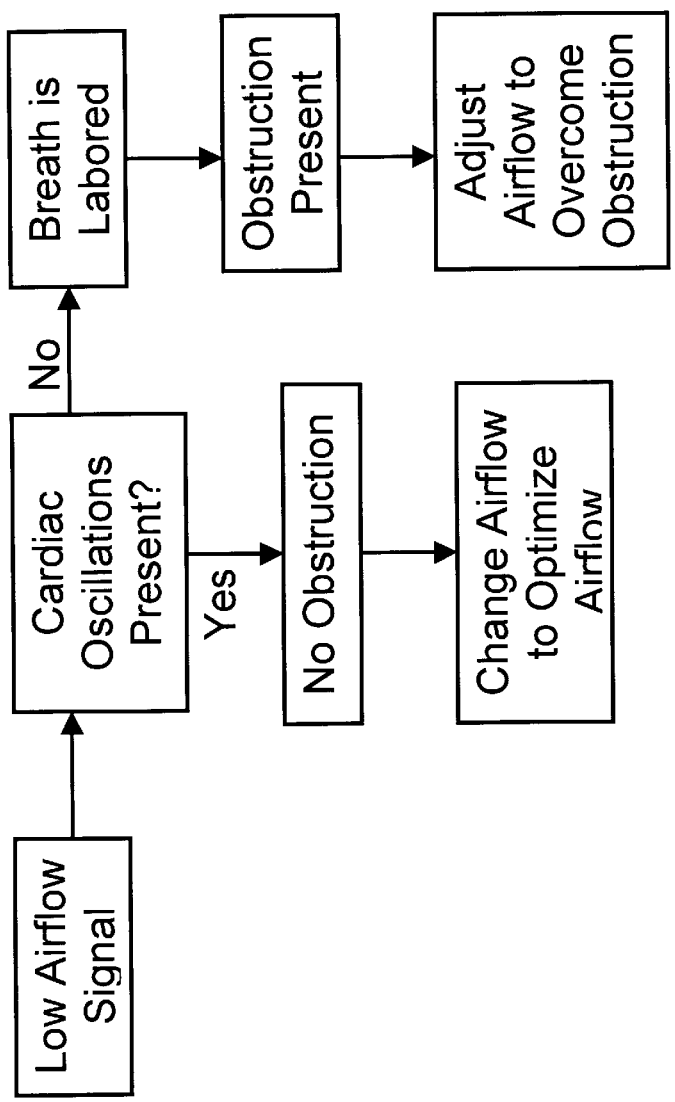
FIG. 8 is a flow diagram showing the improvement in detecting the presence or absence of cardiogenic oscillations in the airflow of a patient.

One method for adjusting the CPAP pressure is illustrated in U.S. Pat. No. 5,803,066. One method for adjusting the CPAP pressure in accordance with the invention is shown in FIG. 5. After the CPAP mask has been fitted to a patient and the CPAP generator has been connected to the mask (step 500), the CPAP pressure is set at a starting pressure. This pressure is determined by patient preference to ease the patient in falling asleep. It may be either a low pressure to minimize discomfort or the patients; previous therapeutic level for those used to a higher pressure at sleep onset. In addition, a time based hold at this pressure may be incorporated. After a settling period of about 30 seconds (step 501), the flow signal is analyzed.

If it is determined that flow limitation has occurred (step 503) and that CPAP pressure is less than the maximum allowed (step 504), then the CPAP pressure is increased by 0.5 cm $H_2O$ (step 505) and the method returns to the settling step (step 501) for further processing. If at the pressure comparing step (step 504) the pressure was not less than the maximum allowed CPAP pressure, then the method returns to the settling step (step 501) without increasing the CPAP pressure.

If it was determined that a flow limitation was not present (step 503), then a determination is made (step 46) whether a predetermined time has elapsed following the last change in the CPAP pressure. The predetermined time may be, for example, two minutes. If the predetermined time has not elapsed, then the method returns to the settling period step (step 501). If the predetermined minimum time has elapsed, it is determined whether CPAP pressure is greater than the minimum allowed pressure (step 507). If it is greater than the minimum allowed pressure, then the CPAP pressure is decreased by 0.5 cm $H_2O$ (step 508), and the method returns to the settling step (step 501). Otherwise, the method returns to the settling step (step 501) without decreasing the CPAP pressure.

While the above described example used CPAP pressure change steps of 0.5 cm $H_2O$, it is apparent that the invention is not limited to pressure changes of this magnitude. In addition, the pressure changes need not necessarily be equal throughout the range of adjustment.

Similarly, a flow limitation determination step may involve any of a number of waveform analysis procedures. For example, the signal corresponding to the airflow/waveform maybe differentiated in the portions thereof corresponding to inspiration. A markedly peaked result from such differentiation indicates the presence of flow limitation, as is evident from an analysis of differentials of waveforms created. Alternatively, the waveform may be analyzed for the presence of harmonics of the cyclic rate of the waveform in the inspiration period thereof, since the presence of a significant amplitude of harmonics of the cyclic rate (i.e., the breathing rate) indicates the presence of a waveform indicative of flow limitation. It is evident that analyses of this type may be effected by conventional hardware or software. The invention, however, is not limited to the above specific techniques for determining divergence of the waveform from the normal non-flow limited waveform to a waveform indicating the presence of flow limitation.

The optimizing method for determining whether to increase or decrease the controlled positive pressure when the waveforms are unambiguous is described in U.S. Pat. No. 5,803,066. The optimizing method for determining whether to increase or decrease the controlled positive pressure comprises several steps. The first step is to detect the presence of a valid breath and store data values corresponding to an inspiratory flow waveform of that breath for further analysis. Alternatively, flow data values may be stored for the entire breath. Next, the stored breath waveform is analyzed regarding its shape for presence of flow limitation. Whether flow limitation is present is in art determined by flow limitation parameters calculated from the shape of the waveforms of the current breath and of the immediately preceding breath. Once the presence of flow limitation has been analyzed, the system determines an action to take for adjusting, the controlled positive pressure. The pressure setting is raised, lowered, or maintained, depending on whether flow limitation has been detected and on the previous actions taken by the system.

The optimizing method has several input parameters which are used in determining the action to be taken during the automatic adjustment mode. For example, the initial controlled positive pressure, or "start value", must be available for use when power-on occurs in the breathing device. Similarly, the method requires a "therapeutic level" of controlled positive pressure to return to whenever an exception condition is detected, such as high constant flow. If the method cannot determine with reasonable certainty that breathing is present, it returns the controlled positive pressure to the prescribed therapeutic level. Also, a "low limit" and a "high limit" are required to determine the minimum and maximum controlled positive pressure level the system will generate when operating in the automatic adjustment mode. The method cannot cause the controlled positive pressure to exceed the maximum or minimum limits of pressure. A prescription pressure can be set which can modify the pressure response based on the relationship between this prescription pressure and the actual currently generated pressure. This serves to bias pressure changes toward the therapeutic pressure.

The method or optimizing the controlled positive pressure includes a first step of detecting a valid breath. A valid breath is determined by a cyclical fluctuation in the respiratory signal superimposed on the constant system leak. This detection is implemented using a three phase state machine with states corresponding to the phases of patient respiration. As is well known in the art, the logic for the state machine may be programmed into the software of a microprocessor or similar computer hardware.

The total flow signal present within the positive pressure flow generator is used as a basis for the breath detection method steps. The breath detection method produces measured data corresponding to the inspiratory flow waveform. Similarly, the breath detection method estimates the constant leak flow and determines several breath description parameters which are described in more detail below. These measured and calculated data form the input to the flow limitation detection step of the optimizing method.

The state machine uses the actual flow signal from the controlled positive pressure source and two derived reference flow signals to determine state transitions. The first state of the state machine is the inspiratory state (INSP). The second state is the expiratory state (EXP). In the third state, (PAUSE), the state machine is in transition from INSP to WXP or from EXP to INSP. The onset of an INSP state defines the beginning of a valid breath. Likewise, the onset of the next INSP state defines the end of a valid breath.

The first state change is determined by the state machine moving from the PAUSE state to the INSP state. This transition denotes the completion of the preceding breath, which is processed before proceeding to the next breath. The data collected and calculated for a breath is discarded if it does not meet certain preprogrammed minimal time and amplitude criteria. The first transition occurs whenever the system is in PAUSE and the total flow signal exceeds the sum of a calculated average leak value (ALV) plus a calculated safety value (SAFE) used as a dead-band. In addition, the derivative of the flow signal must be greater than a minimum value. These criteria enable the system to differentiate between the onset of inspiration and mere changes in glow leakage in the breathing device.

The average leak value (ALV) is a calculated running average of the actual flow signal modified to reflect the possible absence of an expiratory signal. The estimate of the average leak flow is updated during each of the three phases INSP, EXP, PAUSE. The safety reference value (SAFE) is the level of fluctuation in the flow signal which is considered noise. This is calculated as an average of a fraction of the peak flow in each breath. Alternatively, the total flow signal may be first differentiated and then integrated to remove the constant DC offset component (leak flow) and the value of ALV set to zero. Also, the method steps may be applied to the estimated flow signal output of a CPAP generator (which has the constant leak value subtracted out) and the ALV set equal to zero.

In the second transition (C2), the matching state changes from the INSP state to the PAUSE state. This transition occurs when the system is in the INSP state and the total flow signal drops below the ALV. In the next transition (C3), the state machine changes from the PAUSE state to the EXP state. This transition occurs when the system is in the PAUSE state and the total flow signal drops below the ALV minus SAFE reference value. Lastly, the state machine transitions from the EXP state to the PAUSE state (C4). This transition occurs when the system is in the EXP state and the total flow signal rises above the ALV.

The system performs certain calculations during the phase states (INSP, EXP, PAUSE) and phase transitions (C1, C2, C3, C4). During the inspirtatory phase, the system accumulates and stores measured data of total flow e.g., in a flow buffer. Also during the inspiratory phase, the system determines the maximum inspiratory flow value and the maximum derivative value for the total flow signal. During the expiratory phase (EXP), the system determines the maximum expiratory flow value.

During the first transition (C1), the system determines whether the current breath meets the valid criteria for time and size. At the same time, the system calculates a new safety value (SAFE) as a fraction of the breath size. During the second transitions (C2), the system determines the inspiratory time and calculates the running average of the maximum derivative. During the fourth transition (C4), the system calculates the expiratory time.

The determination of the degree of flow limitation present is based on four shape detection parameters, the sinusoidal index, the flatness index, the respiratory effort index and the relative flow magnitude index. The sinusoidal parameter or index is calculated as a correlation coefficient of the actual total inspiratory flow wave (filtered) to a reference sinusoidal half wave to a reference sinusoidal half wave. The correlation coefficient is an index ranging from 1 (sinusoidal or not flow limited) to 0 (not sinusoidal).

An area ratio provides an index of the truncation of the breath that results form flow limitation and ranges from near 0 (extreme flow limitation) to 1 (no flow limitation). The template is a pure half sine wave such that its period matches the duration of the actual inspiratory total flow data curve and its amplitude is such that the derivative of the template at its positive going zero crossing, matches the initial derivative of the actual inspiratory total flow data curve at its zero crossing.

The flatness parameter is a representation of the degree of flatness (or curvature) present in the total inspiratory flow signal. This index is calculated as a variance ratio of the actual signal around a calculated regression line (actual curvature) and an ideal half sinusoidal signal around the same regression line (curvature standard). The regression (REGR) is calculated using the midportion of the inspiratory flow data, for example, from the end of the first third of the inspiratory portion of the breath to the beginning of the last third of the inspiratory portion of the breath This regression is calculated using least squares techniques. The variance of the actual total inspiratory flow data around this regression line is then calculated for the mid-portion of the inspiration. Likewise, the variance of the miss-portion of a pure half sinusoidal template with matching period and amplitude around the regression line is also calculated. The ratio of these two variance produces the flatness parameter or index which ranges from 1 (sinusoidal) to 0 (flat).

The system calculates the respiratory effort index as the ratio of peak derivative (rate of change of flow with respect to time) of the early inspiratory waveform to the peak flow value of the inspiratory waveform. The peak of the total inspiratory flow waveform is plotted against the peak of the waveform for the derivative of the inspiratory flow. The ratio of the peak values (B/A) is also known as the "effort index." This parameter is useful to detect flow limitation in a patient, because an increased respiratory effort is manifested in an increased slope of the inspiratory flow waveform.

The system calculates the relative flow magnitude index as the peak flow of the inspiratory flow waveform minus the peak flow of the previous inspiratory flow waveforms showing flow-limitation divided by the running average of the peak flows of the non-limited breaths minus the average of the flow-limited breaths. This parameter is calculated as:

$$\text{MINMAX} = \frac{FLOW - MIN}{MAX - MIN}$$

where:
  FLOW is the peak flow rate of the current breath;
  MIN is an average of the peak flow of the 20–most recent normal breaths.

This results in a parameter or index which ranges from 0 (flow limited) to 1 (normal).

The four shape detection parameters described above are calculated for the current valid breath and the values are combined against a mathematical function, such as a logistic regression sum. Similarly, weighting factors may be used, wherein the weight given to one or more of the indices may be zero, positive, or negative. The combined values provide a flow limitation parameter which has a value between 0 and 1 that characterizes the likelihood that the current breath has a shape characteristic of flow limitation. The value of the flow limitation parameter is further modified based on the value of the preceding breaths' flow limitation parameters used as a prior probability, allowing calculation of a posterior probability.

The four shape detection parameters (sinusoidal index, flatness index, respiratory effort index and relative flow magnitude index) are used in a mathematical function to determine a likelihood of flow limitation using a logistic regression equation:

$$p = \frac{e(x)}{1 + e(x)}$$

where p is the probability of flow limitation, e is the base of the natural logarithms. X1, X2, X3, and X4 are the shape detection parameters, B0, B1, B2, B3 and B4 are the weighting coefficients (which may include zero), and $$f(x) = B0 + B1X1 + B2X2 + B3X3 + B4X4$$

The probability of flow limitation p has a limited range from 0 (flow limitation) to 1 (normal) and is valid for all values of the function f(x).

If the flow limitation parameter is between 1 and a predetermined normal reference value e.g., 0.65–0.8, then the breath is classified as "normal." If the flow limitation parameter is between 0 and a predetermined flow limited referenced value, eg., 0.4, then the breath is classified as "flow limited." If the flow limitation parameter is between the normal and flow limited reference values, then the breath is classified as "intermediate."

The probability of flow limitation is then compared to the area ratio index. If the probability index classified a breath as normal, then the breath remains classified as normal if the probability index classifies a breath as flow limited or intermediate, the final classification will be determined by area ratio index. If this ratio is less than some specified value, the breath will be classified as flow limited, and if the ratio is greater than or equal to the specified value, the breath will be classified as normal. As each valid breath is identified, its likelihood of being flow limited is calculated. The flow limitation parameter approaches a value of 1 for a normal breath and 0 for a flow limited breath. In this method, a decision is made as to whether to adjust the controlled positive pressure. This decision depends on three factors:

1. the value of the flow limitation parameter for the current breath;
2. the value of the flow limitation parameters in the receding interval (several breaths);
3. whether the controlled positive pressure has been adjusted (and the direction) in the preceding interval of time.

Generally, if flow limitation is detected, the controlled positive pressure will be raised. Similarly, if no flow imitation is detected for an interval of time, then the controlled positive pressure is lowered to test for the development of flow limitation. The desired effect of the method is for the controlled positive pressure to remain slightly above or below the optimal positive pressure despite changes in the optimal therapeutic level of pressure which may occur over time.

This method uses a decision tree to determine whether to change to controlled positive pressure to the airway of the patient. The steps of this method may be programmed into the software of a microprocessor or similar computer. As part of the decision process, the system calculates a time weighted majority function (MF) form the flow limitation parameter values for a certain number of previous breathes, e.g., three, five, or ten breaths, depending on the type of current breath. Depending on the combination of parameters, the controlled positive pressure is raised or lowered a large (1.0 cm) or small (0.5 cm) step, returned to the value prior to the last change, or left unchanged from the last value.

If there has been no change (NC) in the controlled positive pressure for the past interval, the present breath is normal (N) and the majority function is normal, then the controlled positive pressure is lowered by a large step (LOWER LG). If, however, the present breath is intermediate (I) and the majority function is intermediate or flow limited (FL), then the controlled positive pressure is raised PA a small step (RAISESM). Similarly, if the present breath is flow limited, then the controlled positive pressure is raised a small step if the majoring function is intermediate, and by a large step (RAISE LG) if the majority function is flow limited. Otherwise, no change is made to the controlled positive pressure.

If the controlled positive pressure has been lowered in the past interval, the present breath is normal and the majority function is normal, then the controlled positive pressure is lowered by a large step (LOWER LG). If, however, the present breath is intermediate or flow limited and the majority function is intermediate or flow limited, then the controlled positive pressure is raised to the previous level (RAISE PV). Otherwise, no change is made to the positive pressure.

If the controlled positive pressure has been raised in the past interval, no action is taken for a period of time, e.g., ten breaths. Then if the present breath is normal and the majority function is normal, the controlled positive pressure is lowered by a small step (LOWER SM). Conversely, if the present breath is intermediate or flow limited then the controlled positive pressure is raised by a small step if the majority function is intermediate and by a large step if the majority function is flow limited. Otherwise, no change is made to the controlled positive pressure.

In addition, the detection of apnea is used to initiate the decision to raise the controlled positive pressure. Apnea is detected as the absence of fluctuations in flow that are of sufficient amplitude to present breaths. If an apnea of sufficient duration occurs, then the algorithm first determines whether this presents a true patient apnea or a patient disconnect from the pressure generator. If the average flow rate, as described in the section on breath detection, is greater than some predefined value, then a patient disconnect condition has occurred and the pressure is changed to some absolute, predetermined level and the algorithm then waits for the resumption of breathing. If the average flow rate is below the threshold value, then this represents a true apnea. Once an apnea has been detected it can be further classified as either obstructive or central. This classification is based on the presence (central apnea) or absence (obstructive apnea) of regular, small-amplitude flow pulsations with a frequency in the range of the cardiac frequency. These pulsations can be detected from the flow signal after it is appropriately filtered and transformed to magnify their amplitude. The signal transformation function (which preferentially magnifies the amplitude of the signal near its average value) may include, but not be limited to, non-linear mathematical functions (e.g., square root) and look up tables. These periodic fluctuations are then detected in the transformed signal with variance and/or period amplitude techniques which identify fluctuations at a frequency similar to the cardiac cycle (e.g., 40–120/min). If cardiac frequency oscillations in the flow signal are detected, then the apnea is classified as central. In response to a central apnea CPAP pressure may be increased by a different algorithm than that used for obstructive apnea, or allowed to remain unchanged. If cardiac frequency oscillations are not detected, then the apnea is classified as obstructive and the controlled positive pressure is raised. The controlled pressure is then held at or above this new increased pressure for a predefined period of time. After the defined time period has elapsed, the pressure may decrease below this new pressure is indicated by the absence of flow limitation and apnea. An additional apnea occurring within a predefined time window of a previous apnea will also increase the controlled positive pressure and may set a longer time period during which pressure may not drop below the new controlled pressure.

Alternatively, the controlled positive pressure may be continuously adjusted at a rate set by a slope parameter, e.g., 0.1 cm per two seconds. The slop parameter, both its magnitude and sign, are updated breath by breath or every other breath based upon the classification of the breath as normal or flow limited and previous controlled pressure changes. This allows for continuous adjustment of the controlled positive pressure. The system may prevent decreases in pressure of successive increases in the controlled pressure occur, e.g., if increases have been made on the previous five breaths. In no event can the controlled positive pressure be set below the low limit or above the high limit reference values. An additional modification to the adjustment of CPAP pressure control may be based on the relationship between the currently applied CPAP pressure and the prescription CPAP pressure to bias changes in such a way as to favor changes toward the prescription pressure and raising changes away from it. For instance, when the actual CPAP pressure is greater than the prescription pressure, a limit may be placed on the magnitude of the pressure increase allowed during a specified unit of time. When the actual CPA pressure is lower than the prescription pressure, then no limit is placed on the rate of increase. Likewise, the rate of pressure decrease may be modified by this relationship. However, when the waveforms are ambiguous, additional information is needed to classify the apneas correctly.

Previously described methods of diagnosing and treating obstructive sleep apnea are described in U.S. Pat. No. 5,803,066. As shown in FIGS. 6 and 7, the detection and measurement of breathing flow is made from a tight sealing nose fitting 102 (mask or prongs) configured with a resistive element 106 inserted in the flow stream as breathing, gas exits from and enters into the fitting. The nasal fitting is further provided with a port 108 for connection to a flow or pressure transducer 104. The resistive element causes a pressure difference to occur between the upstream side and the downstream side when air flows through the element. The magnitude of the pressure difference is proportional to the magnitude of the flow of the air through the resistive element. By continuously measuring the pressure difference, the measurement of the airflow through the resistive element is effectively accomplished. In the preferred embodiment, the pressure measurement is made between the inside of the nose fitting and the ambient pressure in the room.

As shown in FIGS. 6 and 7, a nasal prong 102 has been configured with a mesh screen resistor 106 at the air inlet, which creates a pressure signal within the nasal prong proportional to the airflow through the nasal prong. Although the figures show an external pressure transducer 104 coupled to the nose fitting by flexible tubing 108, the pressure transducer could be embedded within the structure of the nose fitting, thereby sensing the pressure difference between the inside and outside of the nose fitting. Pressure and flow data values may be continuously measured and recorded on a data logging device such as a microprocessor having program memory and storage media. Thus, the recorded flow signal may be analyzed during or after collection to categorize breaths as described below.

In this instance, while the patient is using the diagnostic device at home, digitized waveforms are stored in nonvolatile memory such as flash memory, floppy or hard disk, or battery-powered random-access memory (RAM). Additional measurements may optionally be recorded, including patient sleeping position and blood oxhemoglobin saturation level from a device such as a pulse oximeter. Since the value of these two measurements do not change relatively rapidly, the memory storage requirements would not be increased significantly.

After using the diagnostic device to record the desired parameters while sleeping for one or more nights, the patient returns the device or data storage unit to the physician. The physician extracts the data from the storage, and analyze it to determine the amount of flow limitation and apnea present, along with the other two parameters, if they were recorded. The resulting analysis is used to determine whether the patient needs a more detailed sleep study or whether therapy should be started without further studies.

If the decision to start therapy because sufficient flow limitation and/or apnea is present, the patient is provided with a self-adjusting therapy device for home use, of the method described heretofore. The home therapy device also incorporates a recording component which records flow, pressure and one or two optional parameters as described above. After using this therapy device during sleep for one or more nights, the data are returned to the physician. The physician analyzes the data to document the reduction of flow limitation and apnea achieved by the thera device. To document the reduction in $SaO_2$ saturations, desaturation if the optional parameter was recorded, and to determine whether the patient's condition could be effectively treated by a less expensive therapy device which is not self-adjusting.

For diagnosing a patient who reports excessive sleepiness and perhaps also snoring, the patient is instructed how to use the diagnostic device and how to position the sensors. The diagnostic device collects flow data and, optionally, position and/or oximetry data. The data are collected at a rate sufficiently high to capture the details of each waveform.

Other known methods of diagnosing and treating OSAS and other breathing disorders in sleep are described, for example in U.S. Pat. Nos. 5,203,343, 5,245,995, 5,148,802 and 5,433,193, the entire contents of each of which also being incorporated herein by reference. For example, Axe et al. in U.S. Pat. No. 5,203,343, describe a method and device for controlling sleep disorder breathing using variable pressure. A compressor supplies air at a relatively low pressure to the user's air passages while the user is asleep. A pressure transducer will monitor the pressure and convert the pressure into an electrical signal. The electrical signal is filtered and processed to compare it to the characteristics of waveform that exists during snoring. If the envelope of the waveform exceeds an average threshold value in duration and in area, then the microprocessor will consider the envelope possibly associated with a snore. If a selected number of envelopes of this nature occur within a selected time period, then the microprocessor considers snoring to exist and increases the pressure of the compressor. If snoring is not detected within a certain time period, then the microprocessor lowers the level gradually.

Sanders et al., U.S. Pat. No. 5,148,802, treat sleep apnea by applying alternating high and low level positive airway pressure within the airway of the patient with the high and low airway pressure being coordinated with the spontaneous respiration of the patient.

Sullivan et al., in U.S. Pat. No. 5,245,995, discloses a CPAP apparatus including a variable pressured air source and means to vary the air pressure delivered therefrom; a nose piece for sealed air communication with a patient's respiratory system; an air communication line from the air source to the nose piece; a sound transducer adapted to be in sound communication with the patient's respiratory system; and a feedback system controlling the output pressure of the air source in response to an output from the transducer so as to increase the output air pressure from said air source, in response to detection of sound indicative of snoring, in accordance with a predefined procedure. The sound transducer comprises a pressure transducer which, in addition to detecting snoring sounds, can detect other respiratory parameters such as the rate of breathing, inhaled air flow volume, and inhaled air flow rate. Output air pressure for air source is increased in response to one or more of these parameters in accordance with a predefined procedure.

Sanders et al., in U.S. Pat. No. 5,433,193, disclose a method and apparatus for delivering breathing gas such as for treating sleep apnea by applying alternating high and low level positive airway pressure within the airway of the patient. The high and low airway pressure are coordinated with the spontaneous respiration of the patient.

Whichever method is used, there will occasionally be ambiguous readings for the presence of an obstructive event. When the reading, is ambiguous, cardiogenic oscillations supports are detected through standard signal processing techniques, particularly during the inter-breath (expiratory) intervals and during apneas. The presence of cardiogenic oscillations supports the lack of an airway obstruction, while the absence of cardiogenic oscillations supports the existence of a partial obstruction (period of high resistance). This presence/absence of cardiogenic oscillations is used to alter the thresholds used to define "abnormal" flow contours used in classifying breaths as "flow-limited", or which otherwise define obstructed breathing. Thus, with the added information from this analysis, one may successfully reclassify a breath or sequence of breaths having am ambiguous reading as either obstructed or non-obstructed. Once it has been determined that an obstruction is or is not present, appropriate treatment can be administered, such as in any of the manners described in said U.S. Pat. Nos. 5,803,066, 5,203, 343, 5,245,995, 5,148,802 and 5,433,193, as described above in order to modulate the positive airway pressure. The term "modulate the positive airway pressure" is intended to include modulating the continuous pressure, as in conventional CPAP devices, or modulating the expiratory pressure, as in bilevel devices. Usually, when an event is classified as obstructive, the relevant pressure is increased, and when an event is classified as non-obstructive, the relevant pressure remains unchanged or may be decreased.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same function can be used; and it is intended that such expressions be given their broadest interpretation.

REFERENCES

Ahmed, et al (1997), "Cardiac Oscillations on the airflow signal during CPAP as a marker of central apnea", *Am J Resp Crit Care Med*, 155:A131.

Berthon-Jones et al (1996), "Nasal continuous positive pressure treatment: current realities and future", *Sleep*, 19(9) :S131–S135.

Boudewyns et al (1998), "Appearance of central apnea in a patient treated by auto-CPAP for obstructive sleep apnea", *Respir Med*, 92(6):891–893.

Brenner et al (1995), "Determination of DLCO and cardiac output from expired gas slopes with cardiogenic oscillations", *Respir Physiol*, 99(1):147–155.

Issa et al (1996), "Reversal of central sleep apnea using nasal CPAP", *Chest*, 90(2):165–171.

Kryger, M H (1994), "Monitoring respiratory and cardiac function", in M. H. Kryger et al, eds. *Principles and Practice of Sleep Medicine*. W. B. Saunders, Philadelphia, 984–993.

Lauzon et al (1998), "Cardiogenic oscillation during single-breath tests performed in microgravity", *J Appl Physiol*, 84(2):661–668.

Lemke et al (1996), "Use of a magnified cardiac waveform oscillation to diagnose infant apnea: a theoretical and clinical evaluation", *Am J Respir Crit Care Med*, 154:1537–1542.

Lemke et al (1990), "Evidence of a critical period of airway instability during central apneas in preterm infants", *Am J Respir Crit Care Med*, 57:470–474.

Marrone et al (1996), "Occurrence of breathing disorders during CPAP administration in obstructive sleep apnea syndrome", *Eur Respir J*, 4(6):660–666.

Milner et al (1990), "Upper airway obstruction and apnea in preterm babies", *Arch Dis Child*, 55:22–25.

Morrell et al (1995), "The assessment of upper airway patency during apnea using cardiogenic oscillations in the airflow signal", *Sleep*, 18(8):651–658.

Popper et al (1986), "Endoscopic observations of the pharyngeal airway during treatment of obstructive sleep apnea with nasal continuous positive pressure—a pneumatic splint", *West J Med*, 144:83–85.

Rechtschaffen et al (1968), eds., *A manual of standardized terminology, techniques and scoring system for sleep stages of human subjects*. Los Angeles: UCLA Brain Information Service/Brain Research Institute.

Series et al (1997), "Efficacy of automatic continuous positive airway pressure therapy that uses an estimated required pressure in the treatment of the obstructive sleep apnea syndrome", *Ann Intern Med*, 127(8 Pt1):588–595.

Shepard J W (1991). *Atlas of Sleep Medicine*. New York: Futura Publishing Company.

Teschler et al (1996), "Automated continuous positive airway pressure titration for obstructive sleep apnea syndrome", *Am J Respir Crit Care Med*, 154:734–740.

West et al (1961), "Pulsatile gas flow in bronchi caused by the heart beat", *J Appl Physiol*, 58:384–391.

What is claimed is:

1. In a method for optimizing the amount of positive airway pressure to be applied to a patient receiving continuous positive airway pressure, comprising monitoring to determine whether or not breathing is labored due to an obstruction, and modulating the positive airway pressure based on whether or not an obstruction has been detected;

the improvement comprising resolving any ambiguities observed in the monitored breathing by detecting the presence or absence of cardiogenic oscillations between expiratory periods and between breaths in the airflow of the patient and classifying the ambiguous breath as being labored due to an obstruction if cardiogenic oscillations are absent and classifying the ambiguous breath as not being labored due to an obstruction if cardiogenic oscillations are present, and, if cardiogenic oscillations are present, indicating the absence of an obstruction, changing the airflow to the patient to optimize the airflow to the patient, and, if cardiogenic oscillations are not present, indicating the presence of an obstruction, and adjusting the airflow to the patient to overcome the obstruction.

2. The method according to claim 1, wherein said monitoring to determine whether or not breathing is labored due to an obstruction is accomplished by detecting flow limitation by analyzing an inspiratory waveform.

3. In an apparatus for optimizing the positive airway pressure to be applied to a patient, said apparatus comprising a device which applies an initial level of positive airway pressure of a breathing gas to a patient, a device which monitors the breath of the patient during expiratory periods and between breaths to determine whether or nor breathing is labored due to an obstruction, and a device which modulates the positive airway pressure of breathing gas based upon whether or nor labored breathing due to an obstruction has been detected;

the improvement comprising a device which resolves any ambiguities detected in the breathing by detecting the presence or absence of cardiogenic oscillations in the airflow of the patient, and wherein said device classified any ambiguous breath detected as being labored due to an obstruction if cardiogenic oscillations are absent and classifies the ambiguous breath as not being labored due to an obstruction if cardiogenic oscillations are present.

* * * * *